United States Patent
Fuchs

[11] Patent Number: 5,395,032
[45] Date of Patent: Mar. 7, 1995

[54] DISPENSER FOR MEDIA

[75] Inventor: Karl-Heinz Fuchs, Radolfzell, Germany

[73] Assignee: Ing. Erich Pfeiffer GmbH & Co. KG, Radolfzell, Germany

[21] Appl. No.: 255,303

[22] Filed: Jun. 7, 1994

Related U.S. Application Data

[63] Continuation of Ser. No. 934,625, Aug. 24, 1992, abandoned.

[30] Foreign Application Priority Data

Feb. 22, 1989 [DE] Germany .................... 4005527.2

[51] Int. Cl.⁶ .................................... B67D 5/58
[52] U.S. Cl. .............................. 222/190; 222/321; 222/631
[58] Field of Search ................ 222/162, 319–321, 222/340, 386, 387, 631–634, 398, 190, 389; 604/214, 218, 220, 230, 231, 184

[56] References Cited

U.S. PATENT DOCUMENTS

| | | | |
|---|---|---|---|
| 1,777,278 | 9/1930 | Huntington | 222/634 |
| 1,911,972 | 5/1933 | Rose | |
| 2,492,830 | 12/1949 | Bannister | 222/190 |
| 3,045,388 | 7/1962 | Hauser | 43/147 |
| 3,240,396 | 3/1966 | Friedenberg | 222/146 |
| 3,907,206 | 9/1975 | Kondo | 239/357 |
| 4,174,055 | 11/1979 | Capra et al. | 222/319 |
| 4,440,325 | 4/1984 | Treuhaft et al. | 222/402.4 |
| 4,592,721 | 6/1986 | Charlebois | 222/389 |
| 4,703,875 | 11/1987 | Malek | 222/389 |
| 4,778,299 | 10/1988 | Coulter | 222/389 |
| 4,946,069 | 8/1990 | Fuchs | 222/321 |

FOREIGN PATENT DOCUMENTS

| | | | |
|---|---|---|---|
| 2454331 | 11/1990 | France | |
| 1475156 | 7/1970 | Germany | |
| 2337220 | 2/1975 | Germany | |
| 9112895 | 9/1991 | WIPO | 222/320 |

Primary Examiner—Andres Kashnikow
Assistant Examiner—Philippe Derakshani
Attorney, Agent, or Firm—Quarles & Brady

[57] ABSTRACT

A dispenser for dispensing a single dose of a powder medium is incorporated in an essentially hermetically sealed medium chamber with an essentially hermetically sealed compressed air pump. The pump chamber can be opened to the medium chamber through an inlet valve only after a first partial section of the pump stroke, whereupon the compressed air flow fluidizes the powder and expels it in a spurt to the dispenser outlet. A basic body forms an outer housing of elongated cross section with a freely accessible pump cylinder. The dispenser outlet can be easily gripped at the handles with which it is actuated.

28 Claims, 2 Drawing Sheets

DISPENSER FOR MEDIA

This application is a continuation of application Ser. No. 07/934,625, filed Aug. 24, 1992, now abandoned.

BACKGROUND AND SUMMARY OF THE INVENTION

The invention relates to a dispenser for media, which is in particular suitable for a stored medium and a separately stored, identical or non-identical, second, flowable medium having different possible states. Such media can be gaseous or slightly volatile, liquid or pasty, and/or pulverulent.

According to the invention, a manually operable pump is proposed, with at least one pump chamber and with at least one outlet channel leading to a dispensing opening, so that the dispenser is simple to use and construct.

The invention avoids the disadvantages of known solutions. The invention is also more particularly directed to a dispenser of the aforementioned type that dispenses or discharges a stored medium with the aid of a further delivery or carrier medium.

The dispenser includes a chamber, in which a precise dose of a first medium, in a fresh form, is stored and protected over a long period of time. The chamber is substantially tightly sealed in its starting position. The chamber is connected in line with the pump and the pumped medium flows through the chamber during operation. The stored medium is dispensed from the medium chamber and is optionally delivered in a single pump stroke to the dispensing opening. If the stored medium is a pulverulent medium, then it is appropriately fluidized with a gaseous pumping medium and is forced from one end of the medium chamber and out through the opposite end.

The pumping medium can be pressurized in a first partial stroke from the starting position to the point where the connection is opened to the medium chamber. Appropriately the medium chamber is located on the pressure side and not the suction side of the pump, so that the stored medium does not flow through the pumping chamber. By an appropriate control the medium chamber can be opened prior to the start of the pump stroke at the inlet and/or at the outlet by a suitable sequence control. If it is necessary to overcome a resilient catch by applying a corresponding operating pressure to initiate the pump Stroke, this automatically leads to a sudden operation of the pump and therefore to the dispensing of the medium in a single spurt. For obtaining higher flow rates of the pumping medium, the connecting channel between the pump chamber and the medium chamber has much smaller passage cross-sections than one or both chambers, the passage cross-sections possibly decreasing in the medium chamber direction.

The cross-sectional storage area of the medium chamber has at least one interruption or at least one filler located within its outer circumferential boundary, so that the stored medium, despite the large dispensing volume, forms only relatively small solid sections.

Advantageously, the dispenser is constructed in such a way that it can be carried and simultaneously reliably operated with the fingers, or with three fingers of one hand, and can be used, for example, in the manner of an oral spray. The dispenser can be constructed as a disposable dispenser which, following the emptying of the medium chamber, does not have to be refilled and can therefore be constructed as a simple standard component, which receives the pump, the stored medium, the channels and optionally, valves or closures within an outer casing, which in side view can be roughly T-shaped or Y-shaped. If the dispenser, namely the pump chamber and medium chamber, is to be emptied in a single pump stroke in successive portions or in one complete pump stroke, and is not to be refilled, then both chambers can be substantially tightly closed with respect to the outside in the starting position and the pump chamber requires no valve and at least no inlet valve. In some embodiments, a medium chamber can be constructed in one piece with a one-piece construction of a pump chamber forming a pump cylinder. In some embodiments, a further medium chamber can optionally be provided in at least one component separate from the pump chamber, for example, with at least one boundary forming a standard component with a pump piston and/or with at least one boundary forming a one-piece standard component with a casing or basic body of the dispenser, with an outlet channel or the like.

In an axial view, the dispenser is suitably elongated, so that it forms one or two facing flat sides passing into one another via two opposite edges of tight curvature permitting the dispenser to find its most stable position on the flat sides, so that it preferably assumes the corresponding horizontal position. If, in this case, the operating handles are positioned transversely to the horizontal plane and are freely accessible and remote from one another, whilst optionally being axially spaced, then the dispenser can easily be gripped at its handles and can also be operated with the fingers assuming the same gripping position. Both facing flat walls of the casing can be traversed by thumb engagement openings, which together form a receptacle for a thumb, so that all the functional parts of the dispenser are protected substantially completely within the casing. The dispenser has thin thumb cutouts which at an end remote from the dispensing opening, form a fork with two substantially rigid and roughly parallel, freely projecting fork fingers. This allows the dispenser, particularly after operation, to be carried in the manner of a clip on the finger or thumb, which facilitates manipulations immediately following dispensing.

Said parts of the pump and/or the medium chamber can, be fixed by means of a plug connection to a basic body, preferably at least as one closed standard unit, which preferably forms the outer casing. In the interior, the plug connection has a projecting plug tongue, with which the standard unit is connected roughly in the direction of the pump operation. It is also possible to have two piston-like components or the like spaced from one another on a shaft, which is guided in a bore narrower than the piston, so that the associated standard component is limited by stops in both displacement directions. In one direction the displacement of the associated piston can at least partly be limited by the stored medium. At least one opening of the medium chamber, or its outlet and/or inlet can, in a substantially valve-free manner, be closed solely by operation of a labyrinthine channel or the like. The stored medium only flows through such a labyrinthine channel when it is under a correspondingly high operating pressure or has been transported by a carrier medium.

These and other features of the invention will be apparent from the disclosure provided by the claims, the description and the drawings, which follow. In the description, reference is made to the accompanying drawings, which form a part hereof, and which illustrate examples of the invention. Such examples,, however, are not exhaustive of the various embodiments of the invention and, therefore, reference is made to the claims which follow the description for determining the scope of the invention.

DETAILED DESCRIPTION OF THE PREFERRED EMBODIMENTS

Figure 1:
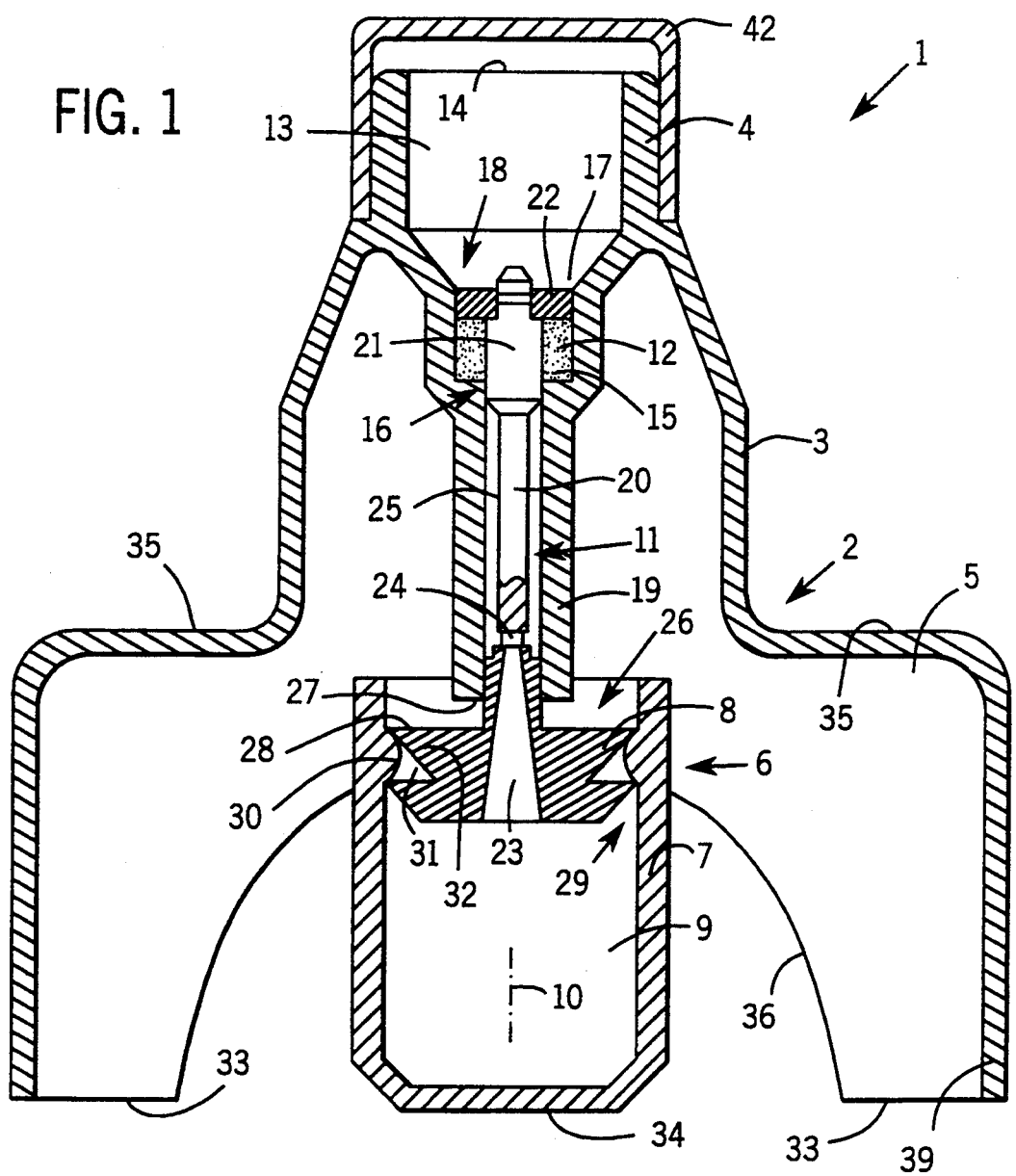
FIG. 1 is an axial section view of a preferred embodiment of the invention.

The dispenser 1 has a hollow basic body 2, with a freely projecting neck 3 that forms a connecting piece 4 at an end remote from a widened casing 5 that projects to all sides beyond the circumference of the neck 3. Within the cap-like casing 5, having a hollow lower end and neck 3, there is positioned a thrust piston pump 6. Pump 6 has a one-piece, cup-shaped, substantially cylindrical cylinder 7 and a piston 8 mounted therein, which can be moved from a fixed starting position to create a vacancy that defines a pump chamber 9 sometimes referred to herein as an auxiliary chamber. All said components and arrangements are located on a common central axis 10, along with an outlet channel 11, a medium chamber 12, a dispensing chamber 13, an outlet opening 14, an inlet 15, an inlet valve 16, an outlet 17, an outlet valve 18, a tube 19, a piston shaft 20, a closure body 21, a closure body 22 and/or channel portions 23, 24, 25. All the explained shapes, positions and sizes can be provided accurately or approximately in accordance with the details, or can even differ from the latter.

The outlet channel 11 connects the medium chamber 12 to the pump chamber 9 after opening the inlet valve 16. The outlet channel 11 is substantially bounded by the one-piece standard unit formed by the piston 8 and the piston shaft 20. The cylindrical medium chamber 12 is provided within a widened transition portion of tube 19, which extends down from the junction of connecting piece 4 and neck 3, and is otherwise spaced apart from the neck 3. The medium chamber 12 is located immediately adjacent to the rear end of the connecting piece 4 and passes into the latter via a funnel-shaped widened transition portion. The external diameter and the capacity of the medium chamber 12 are smaller than those of the pump chamber 9 and the chamber 13 bounded by the connecting piece 4, said chamber 13 being larger than the chamber 9. The front end of the outlet chamber 13, which is open to the full width forms the outlet opening 14.

To the rear end of the medium chamber 12 is connected a shoulder portion of the tube 19 that is reduced in cross-section. A bore that enters chamber 12 is sealed by the piston shaft 20 sliding therethrough. The piston shaft 20 forms or carries two valve or closure bodies 21, 22 with which are closed the inlet 15 located at the front end of the outlet channel 11 and the opposite outlet 17 in the starting position according to FIG. 1 and are opened following a first operating phase. The closure body 21 is formed by a widened portion of the piston shaft 20. A tubular channel 25 is formed between the portion of the piston shaft 12 and the wall of tube 19 located below the shoulder of tube 19. At a lower end of this channel portion 25, a piston shaft 12 has a groove forming a transverse channel 24 connecting channel portion 23 and channel portion 25. Channel 23 is tapered in an acute-angled manner in the direction of flow and opens through the rear or bottom face of piston 8 into the pump chamber 9. The other closure body 22 is located on the front end of the piston shaft 20 and includes a disk or ring body, whose outer circumference engages in slideable sealing manner on the inner cylinder surface formed by the medium chamber 12.

A sequence control 26 is provided for opening the outlet valve 18 of the medium chamber 12 immediately following start of the operation of the pump 6. The front end face of the tube 19 forms a driving surface 27 that faces a stop face 28 on the pump piston 8 along an idling path, which is located along a common axis with the opening path of the outlet valve 18. When the cylinder 7 is moved as an operating unit, in the operating direction, it carries the piston 8 with it up to the engagement of the faces 27, 28, which leads to the simultaneous opening of the valves 16 and 17. On further movement, the pump 8 in the cylinder 7 is moved in the pumping direction, so that air passes out of the pump chamber 8 through the outlet channel 11 with an increased flow rate. The air passes through the inlet 15 and into the medium chamber 12 and from there, carrying with it the stored medium, through the outlet 17 into the turbulence of outlet chamber 13 and then passes through the outlet opening 14. In the open position, the closure body 22 in the outlet chamber 13 faces the outlet 17 as a baffle plate, so that there is a turbulence of the medium upon passing into the outlet chamber 13. At the end of the pump stroke, the piston 8 engages on the bottom of the cylinder 7, which is located largely within the neck 3.

A locking or catch mechanism 29 is provided for the reciprocal positional securing of the cylinder 7 and the piston 8 in the starting position, The catch mechanism 29 is positioned on the inner circumference of the cylinder 7 and at a limited distance from said open end. A toroidal locking cam 30 is positioned in a circular locking groove 31 on the outer circumference of the piston 8. The locking groove 31 is formed by an intermediate groove between two axially adjacent piston lips 32, which are constructed in one piece with the piston 8 or the piston shaft 20 to provide, when viewed in axial cross-section, an acute-angled toothed profile. The interengaging locking members 30, 31 bring about a hermetically sealed closure of the pump chamber 9 in the starting position. It is possible to overcome the catch by a correspondingly high pressure, but at least one piston lip is not deformed by the locking cam, whilst an adjacent lip springs over the locking cam 30, whilst maintaining the tight engagement. The control path of the closure body 22 is much shorter than its distance from the outlet opening 14, so that the closure body 22 is set back relatively far behind the outlet opening 14 in all positions. The closure body 22 forms the bottom of the outlet chamber 13 in the staring position.

The piston unit is formed by the pump piston 8 and the piston shaft 20. The separately engaged closure body 22 is exclusively formed by the plug engagement of the piston shaft 20 and the widened portion of tube 19, which substantially completely receives it. The axial securing by the closure body 22 rests on the content of the medium reservoir 12 and is secured against movement in the other direction by the prestressed engagement in the inner circumferential surface, so that a catch is formed which can be overcome with a predetermined force. The cylinder 7 slides freely while engaging the outer circumference of the circular disk-shaped piston 8. Apart from the pump 6 with the support shaft 19, the basic body 2 is completely free from internal components, such as, for example, reinforcing ribs or the like, so that, although the basic body 2 is substantially dimensionally rigid, it can be elastically compressed at its rear end transversely to the central axis 10.

On the rear end of the casing 5, open to its full width, the basic body 2 forms two planar end faces 33 at right angles to the central axial 10. As seen in FIG. 1, the cylinder 7 is spaced between the two planar end faces 33. The outside of the bottom of the cylinder 7 forms a finger pressure surface or handle 34, which is slightly set back with respect to the plane of the end faces 33 in the starting position. As a result, the dispenser 1 can be placed in an unimpeded manner with the end faces 33 resting on a base.

In the jacket of the casing 5, there are two facing thumb engagement cutouts 36, which emanate from the end faces 33. The cutouts 36 extend over most of the casing height and width, are identical, aligned, concavely limited and forwardly width-decreasing from the end face 33 and much wider than the diameter of the cylinder 7. The width of the cutouts 36 can be roughly 20 mm or less and their reciprocal spacing is much smaller than this. In axial view the casing 5 is flat elongated with two facing flat walls 37, which are convexly curved and located on either side of a medium plane 40. The radius of curvature of the casing 5 is much larger than the casing thickness transverse to the plane 40. The two flat walls 37 pass into one another through convex and significantly more curved lateral edges 38, which are connected to the partial surfaces of the end faces 33. The two flat walls 37 are located on either side of a medium plane 41, and at right angles to the plane 40, which forms an axial plane through the central axis 10. The casing 5 has flat elliptical cross-sections and projects in axial view on all sides over the outer circumference of the neck 3, which has a substantially circular cross-section.

As a result of the mass distribution and center of gravity, the dispenser 1 is less stable against tilting, when rested on the end faces 33 than when resting on one of the two flat walls 37, and these three positions are the only stable positions. The extension of the casing 5 between the lateral edges 38 is two to three times larger than the extension transverse thereto, the individual faces of the base 33 being approximately U-shaped or V-shaped with legs directed against one another.

The end wall of the casing 5 is connected in one piece to the neck 3, and neck 3 forms handles 35 in the form of finger pressure surfaces, which are in each case formed by an end portion of the elongated end wall that does not project over the outer circumference of the casing jacket. The handles 34, 35 or pressure surfaces, whose maximum spacing in the direction of the central axis 10 is the casing height, are positioned transversely to the two horizontal planes parallel to the central plane 40, so that the dispenser 1 can easily be gripped from the horizontal position using three fingers. The handles 35 are substantially aligned with the partial surfaces of the end faces 33, in whose vicinity the casing 5 has the maximum strength.

As a result of the described construction, the dispenser 1 is substantially T-shaped, with ends of the T-crossweb curving away from the stem of the "T", said ends forming freely projecting, casing fingers providing a V-shaped profile on either side of the cutout 36 and on whose end faces 33 the dispenser can be placed. The external diameter of the cylinder 7 is only slightly smaller than the internal spacing between the flat walls 37. The described casing portions are singly or all substantially dimensionally stable or elastically resiliently bendable. The connecting piece 4 can be closed with a cap-like cover 42, which is so mounted with its jacket on the stepped outer circumference of the connecting piece 4 that its outer circumference passes flush into the outer circumference of the neck 3, which prevents an accidental removal.

Figure 2:
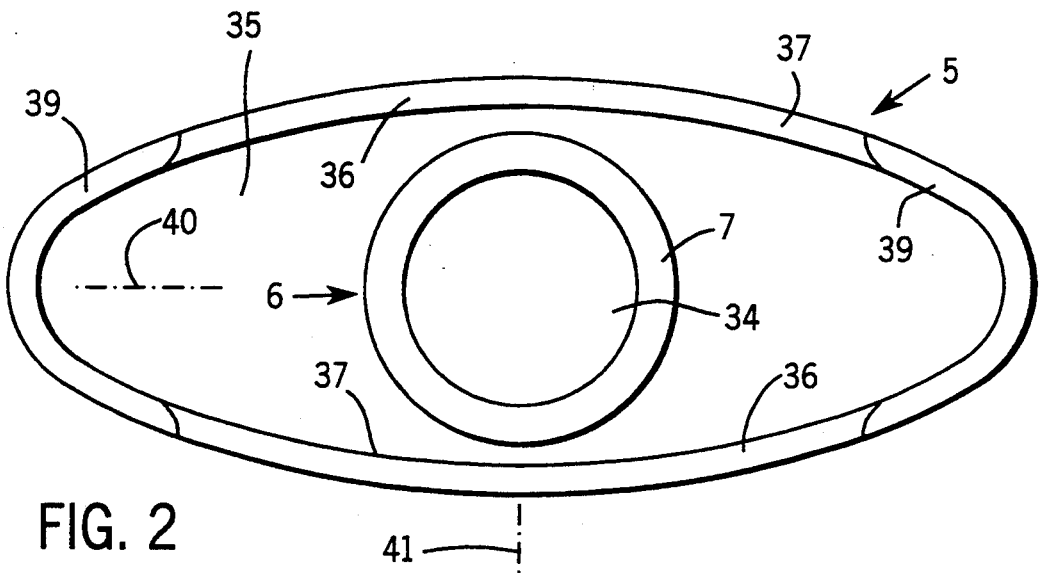
FIG. 2 is a bottom plan view of the dispenser of FIG. 1.
Figure 3:
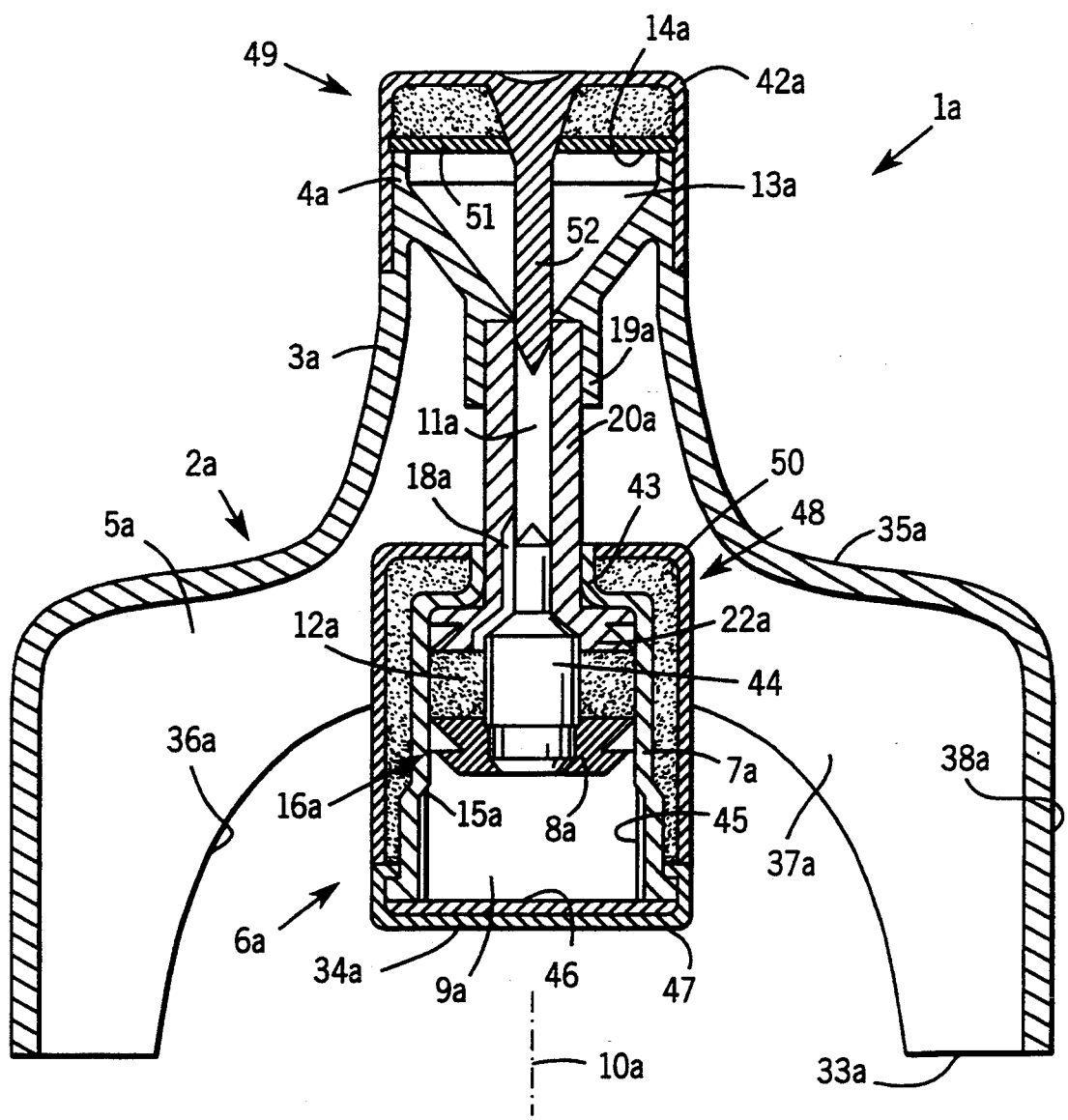
FIG. 3 is another embodiment in a view corresponding to FIG. 1.

In the embodiment in FIG. 3 parts corresponding to parts in the embodiment of FIGS. 1 and 2 carry the same reference numerals, but are followed by the letter "a". The medium chamber 12a is located in this case within a portion of the cylinder casing 7a directly upstream of the pump chamber 9a and is separated from the latter solely by the pump piston 8a. At the other, front end the medium chamber 12a is bounded by a closure piston 22a, which is provided on the same piston unit as the pump piston 8a and is axially movable therewith. Both pistons have the same external diameter and the closure piston 22a in the starting position engages a front end wall of the cylinder casing 7a. In the vicinity of an outwardly projecting guide neck 43, this end wall is traversed by the piston shaft 20a that is directly connected to the closure piston 22a.

Shaft part 44 is inserted in a bore in piston part 22a and piston shaft 20a to form a labyrinthine channel 18a between the piston shaft 20a and shaft part 44. This labyrinthine channel 18a is located on the outer circumference of the shaft part 44. The labyrinthine channel 18a is formed by a multiple, bent inner groove, which extends from the outlet 17a located in the rear face of the closure piston 22a into the outer channel 11a open to its full internal diameter and with respect to its diameter is adapted to the flowabilty of the stored medium. The pump piston 8a can be constructed in one piece with the shaft part 44, or it can be constructed separately for engagement with the shaft 44 of smaller diameter which is inserted in the outlet channel 11a.

The inlet valve 16a is formed on the inner circumference of the cylinder running path where slots 45 are provided, more particularly, longitudinal slots. The pump piston 8 is spaced from the ends of slots 45 to form an inlet 15a in the piston starting position. If the pump piston 8a is moved in the cylinder 7a, then initially the air in the chamber 9a is compressed until all of the piston lips on the pump piston 8a pass over the inlet 15a and are consequently opened in the manner of a slide valve to the following medium chamber 12a. The cylinder casing 7a can have a cylinder body that is open towards the rear end and associated with its bottom. The cylinder casing 7a is closed at this end by a cover 47 which is crimped onto an end flange of casing 7a. Thus, the closure piston 22a can be inserted from this end, preferably together with the shaft part 44, after which the medium to be stored is introduced, the medium chamber 12a sealed by inserting the pump piston 8a, followed by the fitting of the cover 47 and as a result the pump chamber 9a is tightly sealed.

Multi-walled casings 48 or 49 can be provided for keeping at least one stored medium of the dispenser 1a in a dry condition. The casing 48 substantially surrounding the cylinder 7a has a thin-walled outer casing 50 mounted on the cylinder casing 7. Casing 48 is closed at an end wall by the neck 43 and at the other end by engagement with the cover 47.

In said casing 48 is provided a drying agent, which acts both on the content of the medium chamber 12a and on that of the pump chamber 9a. A corresponding casing 49 can be provided in the removable cover 42a to keep dry the interior of the outlet chamber 13a. This casing 49 is bounded by the jacket and the end wall of the cover 42a, as well as by an end wall 51 facing the same and engaging in the jacket. The cover 42a mounts on the end face of the connecting piece 4. In this case the pump 6a is only fixed by the insertion of the piston shaft 20a in the relatively short tubular portion of 19a which is located completely within the neck 3a. The cover 42a can have a closure member 52 that projects over its inside and is also inserted at the associated end of the piston shaft 20a in the outlet channel 11a for automatic withdrawal upon removing the cover 42a.

I claim:

1. A dispenser for discharging two media, comprising:
   a medium chamber providing a medium boundary for receiving a first one of the media, and an auxiliary chamber providing a fluid boundary for receiving a fluid medium defining a second one of the media, and
   an operating unit having an operating shaft that traverses the medium chamber and is displaceable with respect to at least one of said chambers for injecting the second one of the media into said medium chamber and for expelling two media out of said medium chamber,
   wherein said operating unit extends between and separates said medium chamber and said auxiliary chamber, said operating unit providing said medium boundary and said fluid boundary.

2. The dispenser according to claim 1, wherein
said operating unit is manually displaceable with a handle,
said operating unit has an operating shaft, and
said operating shaft has at least one of said boundaries.

3. The dispenser according to claim 2, wherein
said operating unit has a closure member sealingly closing said auxiliary chamber and connected to said operating shaft, and
said operating shaft traverses said medium chamber.

4. The dispenser according to claim 3, wherein said auxiliary chamber and said medium chamber are separated exclusively by said closure member.

5. The dispenser according to claim 1, wherein
said auxiliary chamber is provided by an auxiliary container, and
said medium chamber is displaceable in common with said operating unit with respect to said auxiliary container.

6. The dispenser according to claim 1, further comprising an auxiliary thrust piston pump,
wherein said operating unit provides a piston unit, and
wherein said piston unit has at least one piston including a pump piston of said auxiliary thrust piston pump.

7. The dispenser according to claim 5, wherein
a valve is provided for closing said auxiliary chamber with respect to said medium chamber,
said valve having a valve body displaceable commonly with said operating unit and provided by said operating unit.

8. The dispenser according to claim 7, wherein
said valve body is provided by a closure member mounted in said auxiliary chamber.

9. The dispenser according to claim 7, wherein said valve body is provided by an operating shaft of said operating unit.

10. The dispenser according to claim 1, wherein
said medium chamber defines a chamber end remote from said auxiliary chamber,
said chamber end being bounded by a closure element commonly displaceable with said operating unit to expel the media out of said medium chamber.

11. The dispenser according to claim 1, wherein
said medium chamber has a medium outlet, a baffle member opposing said medium outlet.

12. The dispenser according to claim 11, wherein
said baffle member is displaceable commonly with said operating unit.

13. The dispenser according to claim 1, wherein
control means are provided for opening said medium chamber at an outlet prior to injecting the fluid into said medium chamber.

14. The dispenser according to claim 1, wherein
at least one of said chamber is provided by a container, a base body being provided and displaceable with respect to said container commonly with said operating unit,
said container being connected to said base body exclusively via said operating unit engaging inside said container.

15. The dispenser according to claim 14, wherein
said dispenser defines a central axis,
said base body providing a flattened cap housing of flattened shape when seen parallel to said central axis,
said cap housing substantially entirely receiving at least one of said chambers,
said container being substantially free of contact with said cap housing.

16. The dispenser according to claim 14, wherein
said base body has a neck providing an outlet for the media,
said neck connecting to an end wall providing pressure handles on opposing sides of said neck, a mounting projection being provided inside said neck,
said mounting projection bearing on said operating unit.

17. The dispenser according to claim 14, wherein
said base body bounds said medium chamber.

18. The dispenser according to claim 14, wherein
said base body and at least one of said chambers are interconnected exclusively by at least one reciprocally inserting plug connection.

19. The dispenser according to claim 1, wherein
said auxiliary chamber is free of any inlet for the fluid.

20. The dispenser according to claim 1, wherein
control means are provided for pressurizing the fluid in said auxiliary chamber prior to expelling the fluid into said medium chamber.

21. A dispenser for discharging media comprising
first and second dispenser units reciprocally displaceable by an operating pressure to perform a discharge motion of said dispenser, said dispenser units defining an initial operating state of said dispenser, wherein catch means are provided for holding said first and second dispenser unit, in sad initial operating state against said discharge motion, said catch means defining a force overcomable by increasing said operating pressure, thereby providing control means for initiating said discharge motion in a sudden spurt.

22. The dispenser according to claim 21, wherein said dispenser provides a thrust piston pump, said first dispenser unit providing a pump piston and second dispenser unit providing a pump cylinder displaceable with respect to said pump piston over a pump stroke, said control means being provided for initiating said pump stroke in said sudden spurt.

23. The dispenser for discharging media comprising:

first and second dispenser units reciprocally displaceable to perform a discharge motion of said dispenser, said dispenser units defining an initial operating state, said second dispenser unit providing a fluid chamber bounded by a closure member displaceable with respect to said fluid chamber as a function of said discharge motion, wherein control means are provided for displacing said dispenser units out of said initial operating state over a first partial stroke, said closure member being displaced together with said second dispenser unit, said first partial stroke being followed by said discharge motion for displacing said closure member.

24. The dispenser according to claim 23, wherein said dispenser provides a thrust piston pump, said first dispenser unit providing a piston unit including a pump piston and a piston shaft, said second dispenser unit providing a pump cylinder displaceable with respect to said pump piston, said pump piston providing said closure member, said piston shaft being displaceable with respect to said closure member over said idle path.

25. A dispenser for dispensing media, comprising:

at least one medium chamber for receiving the media in an initial operating state of said dispenser, a cylinder that is axially movable to convey the medium under pressure from the medium chamber, and wherein at least one casing is provided that envelopes said medium chamber and said cylinder for receiving an agent provided to interact with the media in said medium chamber.

26. The dispenser according to claim 25, wherein said agent is a drying agent.

27. The dispenser according to claims 25, wherein said casing is provided on a removable cover detachable from said dispenser.

28. The dispenser according to claim 25, wherein said dispenser has a medium outlet, a closing member being provided for closing said medium outlet, said closing member providing said casing.

* * * * *

UNITED STATES PATENT AND TRADEMARK OFFICE
CERTIFICATE OF CORRECTION

PATENT NO. : 5,395,032
DATED : March 7, 1995
INVENTOR(S) : Fuchs, Karl-Heinz

It is certified that error appears in the above-indentified patent and that said Letters Patent is hereby corrected as shown below:

Column 1, line 49, "Stroke" should be --stroke--.
Column 3, line 3, delete second ",".
Column 3, line 40, "openingthe" should be --opening the--.
Column 8, line 58, "inserting" should be --insetting--.
Column 9, line 4, "sad" should be --said--.
Column 10, line 24, "claims 25" should be --claim 25--.

Signed and Sealed this

Eleventh Day of July, 1995

Attest:

BRUCE LEHMAN

Attesting Officer        Commissioner of Patents and Trademarks